US006878114B2

(12) United States Patent
Murashita (10) Patent No.: US 6,878,114 B2
(45) Date of Patent: Apr. 12, 2005

(54) ULTRASONIC DIAGNOSTIC DEVICE (75) Inventor: Masaru Murashita, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 0 days.

(21) Appl. No.: 10/714,341

(22) Filed: Nov. 14, 2003

(65) Prior Publication Data

US 2004/0127794 A1 Jul. 1, 2004

(30) Foreign Application Priority Data

Dec. 26, 2002 (JP) ........................................ 2002-377976

(51) Int. Cl.[7] .............................................. A61B 8/00
(52) U.S. Cl. ...................................... 600/443; 128/916
(58) Field of Search ................................ 600/440, 441, 600/443, 447; 128/916; 382/195, 199, 203–204, 206; 345/419–427

(56) References Cited

U.S. PATENT DOCUMENTS

| | | | | |
|---|---|---|---|---|
| 5,322,067 A | * | 6/1994 | Prater et al. ................. | 600/443 |
| 5,465,721 A | * | 11/1995 | Kishimoto et al. .......... | 600/443 |
| 5,724,978 A | * | 3/1998 | Tenhoff ....................... | 600/467 |
| 5,871,019 A | * | 2/1999 | Belohlavek .................. | 600/450 |
| 5,911,691 A | * | 6/1999 | Mochizuki et al. ........... | 60/443 |
| 6,106,466 A | * | 8/2000 | Sheehan et al. ............. | 600/443 |
| 6,193,660 B1 | | 2/2001 | Jackson et al. | |
| 6,245,017 B1 | * | 6/2001 | Hashimoto et al. ......... | 600/447 |
| 6,254,540 B1 | * | 7/2001 | Kikuchi et al. .............. | 600/443 |
| 6,282,307 B1 | | 8/2001 | Armato, III et al. | |
| 6,334,847 B1 | * | 1/2002 | Fenster et al. ............... | 600/443 |
| 6,375,616 B1 | * | 4/2002 | Soferman et al. ........... | 600/443 |
| 6,443,896 B1 | * | 9/2002 | Detmer ........................ | 600/445 |
| 6,491,632 B1 | * | 12/2002 | Taylor ......................... | 600/443 |

FOREIGN PATENT DOCUMENTS

JP          2001-37756          2/2001

OTHER PUBLICATIONS

P. Lipson et al., "Deformable templates for feature extraction from medical images", Computer Vision—ECCV 90, First European Conference on Computer Vision Proceedings, Antibes, France, Apr. 23–27, 1990, pp 413–417.

Johannes Behr et al., "Modelling, visualization, and interaction for diagnosis and treatment planning in cardiology", Computers & Graphics, Pergamon Press, Ltd., Oxford, GB, vol. 24, No. 5, Oct. 2000, pp 741–753.

W. Liang et al., "Automated detection of left ventricular borders from intracardiac ultrasound images", Computers in Cardiology, 1996, Indianapolis, IN, US Sep. 8–11, 1996, IEEE Sep. 8, 1996, pp. 265–268.

B. Robert et al., "An Interactive tool to visualize three–dimensional ultrasound data", Ultrasound in Medicine and Biology, New York, NY, US, vol. 26, No. 1, Jan. 2000.

* cited by examiner

Primary Examiner—Francis J. Jaworski
(74) Attorney, Agent, or Firm—Koda & Androlia (57) ABSTRACT

An ellipsoidal axes setting unit sets major and minor axis of an ellipsoid based on cross sectional position information and ellipsoidal parameters input by a user while viewing a display. A major axis end detector unit, a front view minor axis end detector unit, and a side view minor axis end detector unit detect ends of the major and minor axes based on the major and minor axes set at the ellipsoidal axes setting unit and a target tissue surface image for each time phase output from an edge extractor unit. A major/minor axes setting unit selects appropriate lengths of the major and minor axes from the input ends of the major and minor axes and outputs the selected lengths to a region-of-interest generator unit where a three-dimensional region of interest is generated.

18 Claims, 6 Drawing Sheets

TOP VIEW $(X_0, Y_0, Z_0)$

FRONT VIEW

Fig.4

SIDE VIEW

ULTRASONIC DIAGNOSTIC DEVICE

BACKGROUND OF THE INVENTION

1. Field of the Invention

The present invention relates to an ultrasonic diagnostic device and in particular to a three-dimensional ultrasonic diagnostic device in which a region of interest (hereinafter also referred to as "ROI") can be set.

2. Description of the Related Art

In two-dimensional ultrasonic diagnostic devices, the ability to diagnose a target site has been improved by inclusion of a feature allowing the selection of a region of interest ("ROI"). For example, calculation time can be shortened by performing a Doppler calculation for forming a color Doppler image in a selected ROI, while calculation precision can be improved by using only the ROI as the calculation target when an area of a target tissue is to be calculated. The ROI is also employed in three-dimensional ultrasonic diagnostic devices for shortening the calculation time and improving precision of calculation of area or volume (refer to, for example, Japanese Patent Laid-Open Publication No. 2001-37756).

The setting of an ROI in three-dimensional ultrasonic diagnostic devices, however, requires setting of the three-dimensional shape of the ROI and setting of the position of the ROI within a three-dimensional space, and, thus, the setting operation is both complex and tedious for the operator.

SUMMARY OF THE INVENTION

The present invention advantageously simplifies setting of a region of interest within a three-dimensional space.

According to one aspect of the present invention, there is provided an ultrasonic diagnostic device comprising a volume data formation unit for transmitting and receiving an ultrasonic wave to and from a three-dimensional space containing a target tissue to form volume data made of a plurality of voxel data; a reference line setting unit for setting a first reference line passing through the target tissue based on a plurality of planes set within the three-dimensional space and which intersect each other; a boundary finding unit for finding a boundary of the target tissue by referring to voxel data along the first reference line and a second reference line intersecting the first reference line; a shape parameter calculator unit for calculating a plurality of shape parameters for specifying a three-dimensional region of interest related to the target tissue based on the found boundary; and a region-of-interest setting unit for setting the region of interest within the three-dimensional space based on the plurality of shape parameters.

In the above described structure, the boundary of the target tissue defines a site which must be diagnosed, and may correspond to, for example, the surface portion of the target tissue.

With the above-described structure, because the ultrasonic diagnostic device calculates the shape parameters and sets a region of interest based on the shape parameters, setting operation of the region of interest by the user is simplified and the setting of the region of interest within a three-dimensional space is facilitated.

According to another aspect of the present invention, it is preferable that the ultrasonic diagnostic device further comprises a plane image formation unit for forming a plane image containing the target tissue on each of the planes based on the volume data, and that the reference point setting unit sets the reference point based on reference point setting information input by the user using each of the plane images displayed on a display.

With the above-described structure, because the user can set information on a reference point regarding the target tissue while visually observing the position of the reference point, the reference point and, consequently, the region of interest, can easily be set.

According to another aspect of the present invention, it is preferable that, in the ultrasonic diagnostic device, the reference line setting unit sets a slope of the first reference line based on reference line slope information input by the user using each of the plane images displayed on a display, the reference line slope information representing a slope of a projection line of the first reference line projected onto each of the plane images.

With the above-described structure, because a user can set a slope of a first reference line while visually observing the first reference line using a plane image, the setting of the first reference line and, thus, the setting of the region of interest, are both facilitated.

According to another aspect of the present invention, it is preferable that, in the ultrasonic diagnostic device, the reference line setting unit sets a slope of the first reference line based on boundary information of the target tissue obtained using the volume data.

In the above-described structure, the slope of the first reference line may be set, for example, such that the portion of the first reference line within the boundary of the target tissue is maximized or such that the first reference line passes through a specific site of the boundary of the target tissue.

With the above-described structure, it is possible to set a first reference line based on a structure of the target tissue. In other words, this structure allows for setting of a region of interest which reflects the structure of the target tissue.

According to another aspect of the present invention, it is preferable that, in the ultrasonic diagnostic device, the plurality of planes are orthogonal to each other.

With the above-described structure, because the plurality of planes are orthogonal to each other, it is possible to easily comprehend the positional relationship among the planes.

According to another aspect of the present invention, there is provided an ultrasonic diagnostic device comprising a volume data formation unit for transmitting and receiving an ultrasonic wave to and from a three-dimensional space containing a target tissue to form volume data composed of a plurality of sets of voxel data; a plane setting unit for setting three planes which are orthogonal to each other within the three-dimensional space; a first reference line setting unit for setting a first reference line passing through the target tissue based on projected lines of the first reference line projected onto each of two planes of the three planes; a second reference line setting unit for setting a second reference line which is orthogonal to the first reference line in one of the planes onto which the first reference lines is projected; a third reference line setting unit for setting a third reference line which is orthogonal to the first reference line in the other of the planes onto which the first reference line is projected; a reference line end calculator unit for calculating, based on the voxel data, a first reference line end which is an intersection of the first reference line and the boundary of the target tissue, a second reference line end which is an intersection between the second reference line and the boundary of the target tissue, and a third reference line end which is an intersection between the third reference line and the boundary of the target tissue; an axes setting unit for setting a first axis based on the first reference line end and having a predetermined length on the first reference line, a second axis based on the second reference line end and having a predetermined length on the second reference line, and a third axis based on the third reference line end and having a predetermined length on the third reference line; and a region-of-interest setting unit for setting a region of interest having an ellipsoidal shape in the three-dimensional space based on the set first, second, and third axes.

With this configuration, the three planes can be set at arbitrary positions and are set, for example, as an upper plane, a front plane, and a side plane with respect to the target tissue. A plurality of first reference line ends, second reference line ends, and third reference line ends may be provided depending on the shape of the boundary of the target tissue. An example of the target tissue may be an intracardial section within a left ventricle of a heart. In this case, the inner wall of the left ventricle corresponds to the boundary of the target tissue.

With such a configuration, because the shape and position of an ellipsoid is determined based on the first, second, and third axes, it is possible to easily set the region of interest having an ellipsoidal shape within a three-dimensional space.

According to another aspect of the present invention, it is preferable that the ultrasonic diagnostic device further comprises a plane image formation unit for forming a plane image containing the target tissue on each of the planes based on the volume data; and a reference point setting unit for setting, based on reference point setting information input by the user using each of the plane images displayed on a display, a reference point determined based on a structure of the target tissue, and that the first reference line setting unit sets the first reference line passing through the reference point based on a slope angle of the projected line input by the user using each of the plane images displayed on the display, and the second and third reference lines pass through the reference point.

With this configuration, the user can set the reference point and a first reference line at desired positions. In addition, because the ultrasonic diagnostic device sets the region of interest having an ellipsoidal shape based on the setting information, the user can easily set the region of interest at a desired position desired, using a simple procedure.

According to anther aspect of the present invention, it is preferable that, in the ultrasonic diagnostic device, the plane setting unit determines positions of the three planes based on positional information of each plane input by the user; and the plane image formation unit forms, as the plane image, a cross sectional image of the target tissue on each of the planes.

With this configuration, the user can set three cross sectional surfaces on desired positions and set the first reference line based on these cross sectional surfaces.

According to another aspect of the present invention, it is preferable that, in the ultrasonic diagnostic device, the axes setting unit sets, as the lengths of the first, second, and third axes, a length at which each axis exceeds the boundary of the target tissue and projects outside, and the region-of-interest setting unit sets a region of interest having an ellipsoidal shape and surrounding the inside of the boundary of the target tissue.

With this configuration, the ellipsoidal shape which forms the region of interest is set to be larger than the inside of the boundary of the target tissue which is the target to be diagnosed. Because of this, it is possible to set a region of interest which surrounds at least most of, and, more preferably, all of, the section of the diagnostic target.

According to another aspect of the present invention, it is preferable that the ultrasonic diagnostic device further comprises a region-of-interest corrector unit for re-setting the lengths of the first axis, of the second axis, and of the third axes when the inside of the boundary of the target tissue extends beyond the region of interest.

With this configuration, because the region of interest is corrected, the setting precision of the region of interest can be improved, and, as a consequence, precision of diagnosis using the ultrasonic diagnostic device can be enhanced.

According to anther aspect of the present invention, it is preferable that the ultrasonic diagnostic device further comprises an overflow image formation unit for forming an overflow image in which a predetermined display process is applied to the overflowing portion of the inside of the boundary of the target tissue on the surface of the region of interest.

With this configuration, the user can easily observe an overflowing portion of the site to be diagnosed by viewing an overflow image displayed on a display. Thus, this configuration allows for easier estimate of the influences of the overflowing portion to the diagnosis, and, for example, when the user judges that the influences of the overflowing portion to the diagnosis are not significant, it is possible to continue the diagnosis without re-setting the region of interest.

DESCRIPTION OF PREFERRED EMBODIMENT

A preferred embodiment of the present invention will now be described referring to the drawings.

Figure 1:
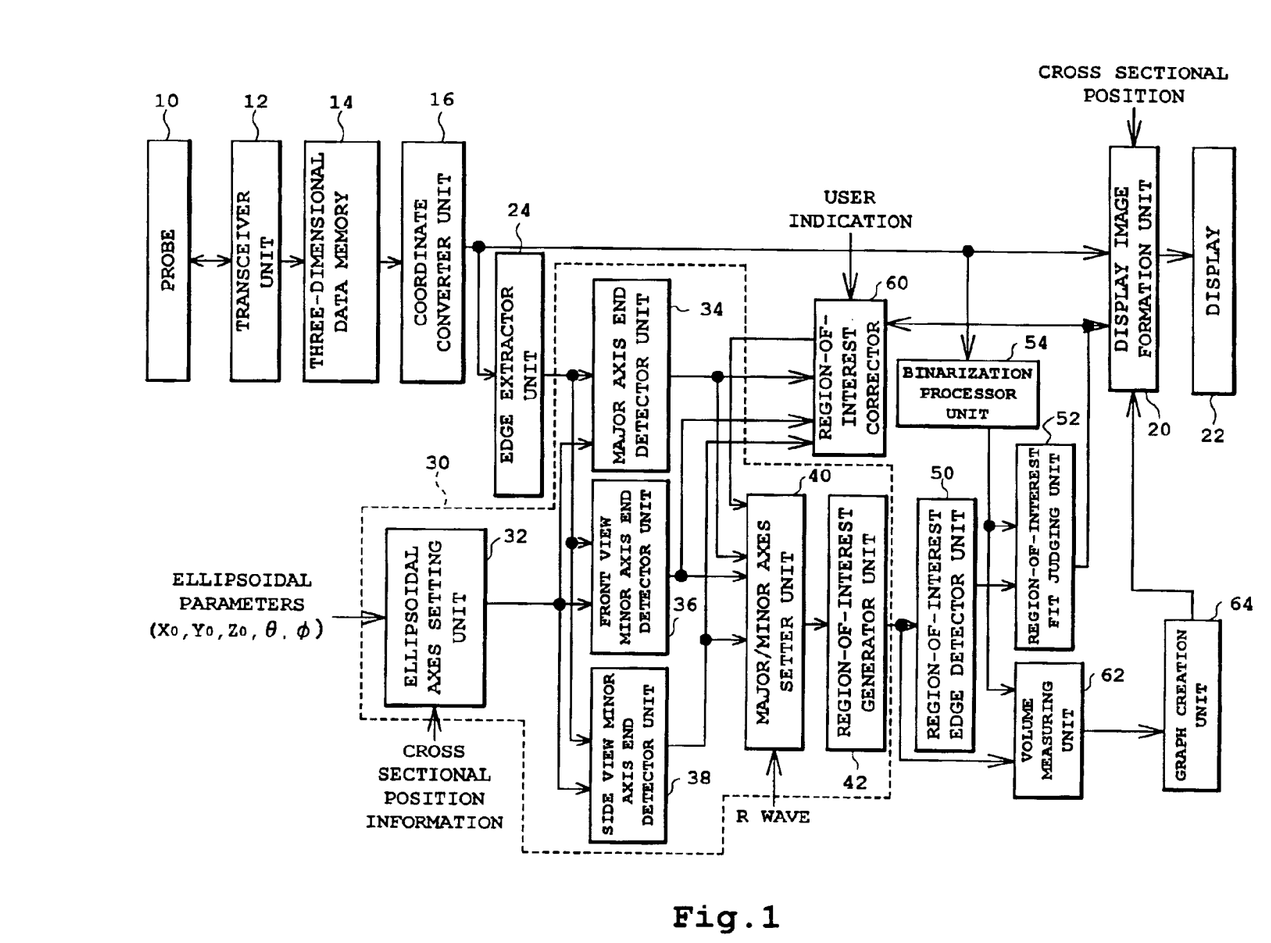
FIG. 1 is a block diagram showing an ultrasonic diagnostic device according to a preferred embodiment of the present invention.

FIG. 1 is a block diagram showing an overall structure of an ultrasonic diagnostic device according to the preferred embodiment of the present invention.

A transceiver unit 12 transmits and receives an ultrasound via a probe 10 into and from a space containing a target tissue to output a three-dimensional ultrasonic image for each time phase to a three-dimensional data memory 14. The three-dimensional ultrasonic image obtained for each time phase is converted, by a coordinate converter unit 16, into a display coordinate system and is output to a display image formation unit 20 and edge extractor unit 24 for each time phase.

The display image formation unit 20 forms a projected image of the three-dimensional ultrasonic image projected on a two-dimensional plane based on the three-dimensional ultrasonic image output from the coordinate converter unit 16 and having converted coordinates. The formation of the projected image may be performed, for example, through a volume rendering method. In addition, the display image formation unit 20 forms a cross sectional image related to a target tissue in the three-dimensional ultrasonic image. Three cross sectional images are formed, one seen from above the target tissue (top view), one seen from the front of the target tissue (front view), and one seen from the side of the target tissue (side view). The positions of the cross sections are set based on cross sectional position information from the user. The projected image and three cross sectional images formed in the display image formation unit 20 are displayed on a display 22 (examples of images displayed on the display 22 are shown in, for example, FIGS. 2–5).

The edge extractor unit 24 extracts a surface image of the target tissue for each time phase based on the three-dimensional ultrasonic image output from the coordinate converter unit 16 and having the coordinates converted. The three-dimensional ultrasonic image is an image formed by normal arrangement of a plurality of voxel data. The edge extractor unit 24 applies a binarization process to the three-dimensional ultrasonic image to distinguish the plurality of voxels into voxels corresponding to the target tissue (target tissue voxels) and voxels corresponding to the sites other than the target tissue (non-target tissue voxels) Then, the edge extractor unit 24 extracts a group of target tissue voxels from among all voxels forming the three-dimensional ultrasonic image, each of which has at least one non-target tissue voxel as an adjacent voxel, and, further extracts a target tissue surface image formed by the extracted group of voxels.

A region-of-interest generating block 30 forms a region of interest having an ellipsoidal shape in the three-dimensional ultrasonic image based on the target tissue surface image output from the edge extractor unit 24 and position information of cross sections and the parameters of the ellipsoid input by the user. The operations of each section of the region-of-interest generating block 30 will now be described referring to FIGS. 2–5. In the following description, structures corresponding to those described in connection with FIG. 1 are assigned the same reference numerals.

Figure 2:
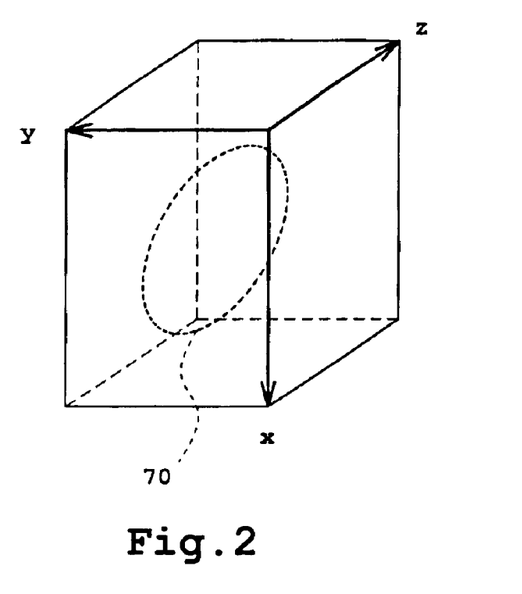
FIG. 2 is a perspective diagram of a three-dimensional ultrasonic image including a three-dimensional region of interest having an ellipsoidal shape.
Figure 3:
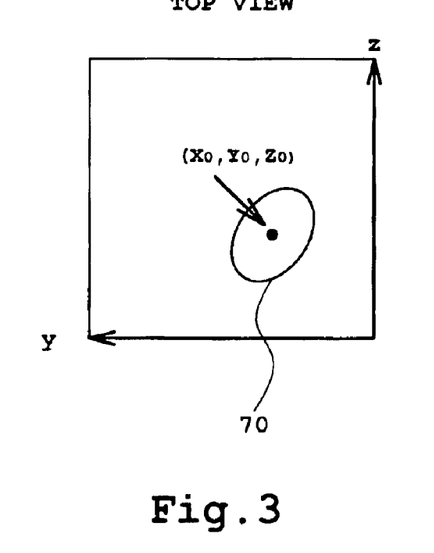
FIG. 3 is a top view showing a three-dimensional ultrasonic image including a three-dimensional region of interest.
Figure 4:
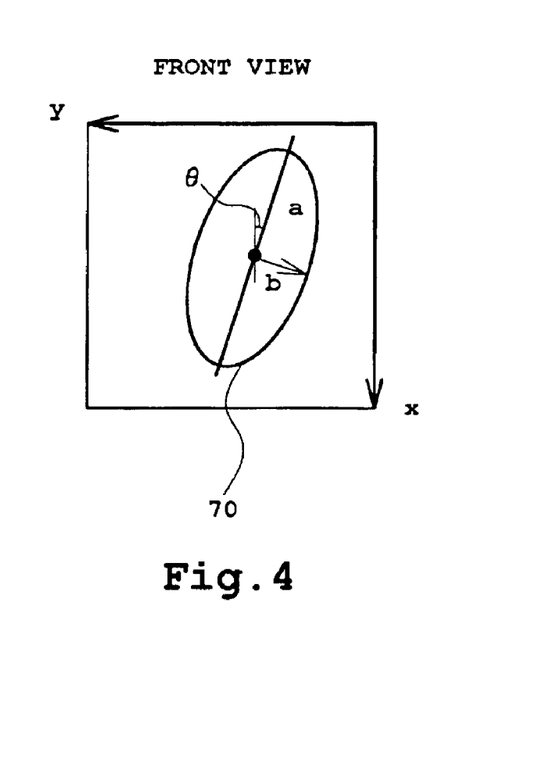
FIG. 4 is a front view showing a three-dimensional ultrasonic image including a three-dimensional region of interest.
Figure 5:
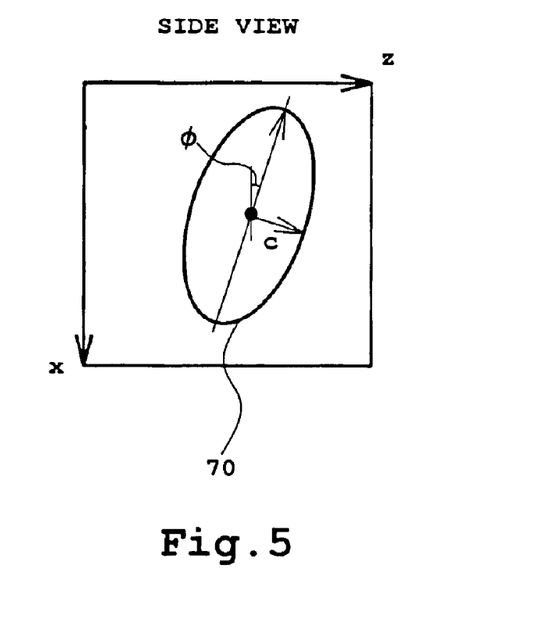
FIG. 5 is a side view showing a three-dimensional ultrasonic image including a three-dimensional region of interest.

FIGS. 2–5 are diagrams for explaining a formation method of a three-dimensional region of interest having an ellipsoidal shape. FIG. 2 is a perspective view of a three-dimensional ultrasonic image including a three-dimensional region of interest 70 having an ellipsoidal shape, in which a target tissue image (not shown) is present. FIG. 3 is a top view of the three-dimensional ultrasonic image including the three-dimensional region of interest 70, FIG. 4 is a front view of the three-dimensional ultrasonic image including the three-dimensional region of interest 70, and FIG. 5 is a side view of the three-dimensional ultrasonic image including the three-dimensional region of interest 70. The "top view" refers to a cross sectional view of the target tissue seen from the above, the "front view" refers to a cross sectional view of the target tissue seen from the front, and the "side view" refers to a cross sectional view of the target tissue seen from the side.

An ellipsoidal axes setting unit 32 sets the major and minor axes of the ellipsoid based on the position information of the cross sections and parameters of the ellipsoid as input by the user. In the setting of the major and minor axes, the user determines the positions of the cross sections shown in FIGS. 3–5. For example, the user may set the position of the top view of FIG. 3 by moving a representation of the cross sectional surface (yz plane in FIG. 2) to a desired position along the x axis direction. Similarly, the positions of the front and side views of FIGS. 4 and 5 can be set to desired positions by the user moving these planes along coordinate axis directions perpendicular to the planes. The position information of the cross sectional planes set by the user is also input to the display image formation unit 20. The display image formation unit 20 forms cross sectional images at each cross section of the three-dimensional ultrasonic image output from the coordinate converter unit 16 based on the positional information of the cross sections. In this manner, images corresponding to the top, front, and side views shown in FIGS. 3–5 are formed in the display image formation unit 20 and displayed on the display 22, which allows the user to set the positions of the cross sections while viewing the cross sectional images displayed on the display 22.

The cross sectional image is used for forming a region of interest that has an ellipsoidal shape and surrounds the target tissue within the three-dimensional ultrasonic image. For this purpose, the positions of the cross sectional planes are set such that the target tissue image within the cross section becomes as large as possible and, more preferably, is maximized. In other words, the user sets the positions of the cross sections such that the cross sectional image of the target tissue at the cross sections becomes as large as possible while viewing the cross sectional image of the target tissue at the cross sections displayed on the display 22.

After the cross sections are set in this manner, the ellipsoidal axes setting unit 32 sets the major and minor axes of the ellipsoid based on ellipsoidal parameter information ($X_0$, $Y_0$, $Z_0$, $\theta$, $\phi$) input by the user. The position of the center of the ellipsoid ($X_0$, $Y_0$, $Z_0$) is set by the user while viewing the three cross-sectional diagrams such that the center is centered, as close as possible, in the cross sections of the target tissues in each cross sectional diagram. For example, the user first sets $Y_0$ and $Z_0$ referring to the top view so that the center becomes the center of the target tissue and then sets $X_0$ referring to the front and side views. Alternatively, it is also possible for the user to set $X_0$ and $Y_0$ referring to the front view and then set $Z_0$ referring to the top and side views, or, to set $Z_0$ and $X_0$ referring to the side view and then set $Y_0$ referring to the top and front views. In this manner, the position of the center of the ellipsoid, that is, a point within a three-dimensional space corresponding to the coordinate ($X_0$, $Y_0$, $Z_0$) is set.

Then, the user sets $\theta$ and $\phi$ which relate to the slope of the major axis of the ellipsoid based on the set position of the center of the ellipsoid. The slope $\theta$ is the slope of the major axis with respect to an x axis in the front view. The user finds the longest line possible and which, more preferably, has a maximum possible length within the target tissue and passes through the center of the ellipsoid in the front view while viewing the image of the front view and sets the slope $\theta$ of this straight line. Similarly, the user finds the longest straight line passing through the center of the ellipsoid, or, more preferably, a maximum length within the target tissue in the side view while viewing the image of the side view and sets the slope $\phi$ of this straight line. In this manner, the major axis of the ellipsoid, that is, a straight line within the three-dimensional space is set corresponding to the coordinates ($X_0$, $Y_0$, $Z_0$) and the slopes θ and φ is set.

The ellipsoidal axes setting unit 32 sets minor axes of the ellipsoid based on the set position of the center and the set major axis of the ellipsoid. Two minor axes are set in planes that pass through the center of the ellipsoid and are orthogonal to the major axis within the three-dimensional space. That is, one straight line in the front view which is orthogonal to the major axis (front view minor axis) and one straight line in the side view which is orthogonal to the major axis (side view minor axis) are set.

In this manner, the ellipsoidal axes setting unit 32 sets the major axis, front view minor axis, and side view minor axis of the ellipsoid which is the three-dimensional region of interest.

Referring again to FIG. 1, a major axis end detector unit 34 detects an end of the major axis based on the major axis set by the ellipsoidal axes setting unit 32 and the surface image of the target tissue for each time phase output from the edge extractor unit 24. That is, the major axis end detector unit 34 calculates, for each time phase, coordinates for a plurality of intersections between the target tissue surface image and the major axis. For example, when the target tissue is of a nearly ellipsoidal shape, two intersections exist between the target tissue surface image and the major axis. The coordinates for a plurality of intersections calculated for each time phase are output to a major/minor axes setter unit 40.

An end detector unit 36 for the front view minor axis detects an end of the front view minor axis based on the front view minor axis set by the ellipsoidal axes setting unit 32 and the surface image of the target tissue for each time phase output from the edge extractor unit 24. That is, the end detector 36 for the front view minor axis calculates, for each time phase, coordinates of a plurality of intersections between the target tissue surface image and the front view minor axis. For example, when the target tissue has a nearly ellipsoidal shape, two intersections exist between the target tissue surface image and the front view minor axis. The coordinates of a plurality of intersections calculated for each time phase are output to the major/minor axes setting unit 40.

An end detector 38 for the side view minor axis detects an end of the side view minor axis based on the side view minor axis set by the ellipsoidal axes setting unit 32 and the target tissue surface image for each time phase output from the edge extractor unit 24. That is, the end detector 38 for the side view minor axis calculates, for each time phase, coordinates of a plurality of intersections between the target tissue surface image and the side view minor axis. For example, when the target tissue has a nearly ellipsoidal shape, two intersections exist between the target tissue surface image and the side view minor axis. The coordinates of a plurality of intersections calculated for each time phase are output to the major/minor axes setting unit 40.

The major/minor axes setting unit 40 sets the lengths of the major and minor axes based on the coordinates of intersections output from the end detector 34 for the major axis, end detector 36 for front view minor axis, and end detector 38 for side view minor axis. Specifically, the major/minor axes setting unit 40 selects, for each time phase, an intersection having a maximum distance from the center of the ellipsoid (major axis intersection) from among the plurality of intersections output from the end detector 34 for the major axis for each time phase. From among the selected major axis intersections selected for the time phases, the major/minor axes setting unit 40 selects the intersection which is most distant from the center of the ellipsoid and sets the distance between the selected major axis intersection and the center of the ellipsoid as the length of the major axis.

In addition, the major/minor axes setting unit 40 selects, for each time phase, the intersection having the largest distance from the center of the ellipsoid (front view minor axis intersection) from among a plurality of intersections output for each time phase from the end detector 36 for the front view minor axis. Then, the major/minor axes setting unit 40 selects the intersection having the largest distance from the center of the ellipsoid from among the front view minor axis intersections selected for the time phases and sets the distance between the selected front view minor axis intersection and the center of the ellipsoid as the length of the front view minor axis.

Moreover, the major/minor axes setting unit 40 selects, for each time phase, the intersection having the largest distance from the center of the ellipsoid (side view minor axis intersection) from among a plurality of intersections output for each phase from the end detector 38 of the side view minor axis. Then, the major/minor axes setting unit 40 selects the intersection having the largest distance from the center of the ellipsoid from the side view minor axis intersections selected for the time phases and sets the distance between the selected side view minor axis intersection and the center of the ellipsoid as the length of the side view minor axis.

The major/minor axes setting unit 40 selects a maximum length for the axes from a plurality of time phases. When the target tissue is a ventricle of a heart, for example, because a heart ventricle repeatedly expands and contracts as the heartbeats, it is preferable that the major and minor axes be set at a telediastolic point. Because a telediastolic moment can be recognized by an R wave of the cardiographic waveform, the lengths of the major axis, of the front view minor axis, and of the side view minor axis are selected based on the time phase when the R wave is generated.

A region-of-interest generator unit 42 generates a region of interest having an ellipsoidal shape based on the lengths of the major axis, of the front view minor axis, and of the side view minor axis output from the major/minor axes setting unit 40. The ellipsoid generated by the region-of-interest generator unit 42 can be represented by the following general formula.

$$\frac{x^2}{a'^2} + \frac{y^2}{b'^2} + \frac{z^2}{c'^2} < 1 \qquad \text{[Equation 1]}$$

Equation 1 shows a general formula of an ellipsoidal region having the center at the origin, radius of major axis of a', and two radii of the minor axes of b' and c'. In other words, a three-dimensional region of interest having an ellipsoidal shape and the center at the origin within a three-dimensional space is determined based on Equation 1 by setting the parameters a', b', and c'. That is, by substituting the values of the lengths of the major axis, of the front view minor axis, and of the side view minor axis output from the major/minor axes setting unit 40 into the parameters a', b', and c' in Equation 1, it is possible to set the outer periphery of the target tissue having an ellipsoidal shape with the center at the origin. Because it is desirable to have a slightly larger region of interest than the target tissue, it is possible to substitute, for example, a value which is approximately 10% to 20% greater than the selected lengths of the major axis, of the front view minor axis, and of the side view minor axis into a', b', and c'. The ellipsoid represented by Equation 1 has its center at the origin. Based on Equation 1, a more general formula can be formed in which the ellipsoid is rotated about the Z axis by θ and about the Y axis by φ, and the center is translated to a position ($X_0$, $Y_0$, $Z_0$).

A conversion for rotating a point P (x, y, z) about the Z axis by an angle of θ can be represented by the following matrix equation.

$$[X \ Y \ Z \ 1] = \begin{bmatrix} \cos\theta & -\sin\theta & 0 & 0 \\ \sin\theta & \cos\theta & 0 & 0 \\ 0 & 0 & 1 & 0 \\ 0 & 0 & 0 & 1 \end{bmatrix} [x \ y \ z \ 1] \quad \text{[Equation 2]}$$

A conversion for rotating a point P (x, y, z) about the Y axis by an angle of φ can be represented by the following matrix equation.

$$[X \ Y \ Z \ 1] = \begin{bmatrix} \cos\phi & 0 & -\sin\phi & 0 \\ 0 & 1 & 0 & 0 \\ -\sin\phi & 0 & \cos\phi & 0 \\ 0 & 0 & 0 & 1 \end{bmatrix} [x \ y \ z \ 1] \quad \text{[Equation 3]}$$

From the above equations, a conversion to rotate a point P (x, y, z) about the Z axis by an angle of θ and then about the Y axis by an angle of φ, and to translate to a position ($X_0$, $Y_0$, $Z_0$) can be represented by the following matrix equation.

$$[X \ Y \ Z \ 1] = \begin{bmatrix} \cos\theta & -\sin\theta & 0 & 0 \\ \sin\theta & \cos\theta & 0 & 0 \\ 0 & 0 & 1 & 0 \\ 0 & 0 & 0 & 1 \end{bmatrix} \begin{bmatrix} \cos\phi & 0 & -\sin\phi & 0 \\ 0 & 1 & 0 & 0 \\ -\sin\phi & 0 & \cos\phi & 0 \\ 0 & 0 & 0 & 1 \end{bmatrix} [x \ y \ z \ 1] + \begin{bmatrix} 1 & 0 & 0 \\ 0 & 1 & 0 \\ 0 & 0 & 1 \\ X_0 & Y_0 & Z_0 \end{bmatrix} [x \ y \ z \ 1] \quad \text{[Equation 4]}$$

By applying the conversion Equation 4 to Equation 1, it is possible to rotate the ellipsoid represented by the Equation 1 about the Z axis by an angle of θ and about the Y axis by an angle of φ and then translate the center to a position ($X_0$, $Y_0$, $Z_0$). The region-of-interest generator unit 42 generates a three-dimensional region of interest having an ellipsoidal shape within the three-dimensional ultrasonic image using Equations 1 and 4 and based on the lengths of the major axis (a'), of the front view minor axis (b'), and of the side view minor axis (c') output from the major/minor axes setting unit 40 and ellipsoidal parameter information ($X_0$, $Y_0$, $Z_0$, θ, φ) set by the user.

A three-dimensional region of interest having an ellipsoidal shape is output from the region-of-interest generating block 30 to an edge extract or unit 50 for the region of interest, which extracts the surface image of the region of interest. The surface of the region of interest can be obtained by applying the conversion equation of Equation 4 to an equation derived from Equation 1 by changing the inequality relation to an equality relation.

A fit judging unit 52 for the region of interest judges whether or not the target tissue falls within the region of interest based on the surface image of the region of interest output from the edge extractor unit 50 for the region of interest and a binarized image of the three-dimensional ultrasonic image output from the coordinate converter unit 16, binarized by a binarization processor unit 54. The binarized image output from the binarization processor unit 54 is an image wherein voxels corresponding to the target tissue (target tissue voxels) and the voxels corresponding to the sites other than the target tissue (non-target tissue voxels) are distinguished. The fit judging unit 52 for the region of interest compares the surface image of the region of interest with the binarized image. When a target tissue voxel is present on the surface image of the region of interest, the fit judging unit 52 for the region of interest judges that the target tissue image extends beyond the region of interest. The fit judging unit 52 for the region of interest creates an image in which the target tissue voxel portion on the surface image of the region of interest is explicitly shown, that is, extension of the target tissue beyond the region of interest is explicitly indicated by, for example, applying a coloring process to the extended region and outputting the thus-generated image to the display image formation unit 20. In addition, the fit judging unit 52 for the region of interest also outputs the image of the overlapping surface region to a region-of-interest corrector 60.

The region-of-interest corrector 60 is a structure for correcting the region of interest when the target tissue extends beyond the region of interest. The region-of-interest corrector 60 will be described below, while referring to FIG. 6.

Figure 6:
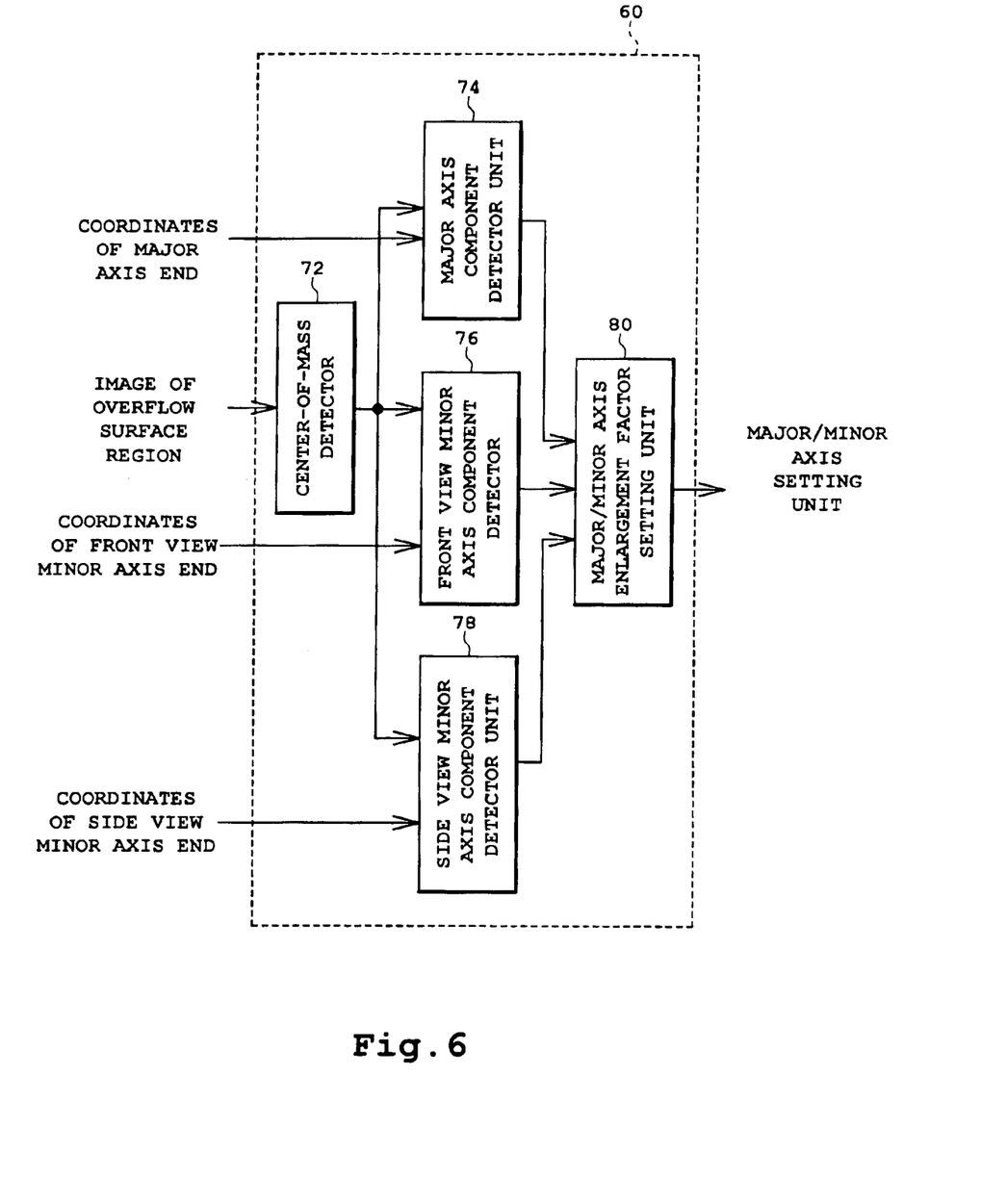
FIG. 6 is a block diagram showing an internal structure of a region-of-interest corrector.

FIG. 6 is a block diagram showing an internal structure of the region-of-interest corrector 60. The region-of-interest corrector 60 comprises a center-of-mass detector unit 72, a major axis component detector unit 74, a front view minor axis component detector unit 76, a side view minor axis component detector unit 78, and a major/minor axes enlargement factor setting unit 80. The image of the surface region output from the fit judging unit 52 for the region of interest is input to the center-of-mass detector unit 72. An image of the surface region extending beyond the region of interest is formed for each time phase and the center-of-mass detector unit 72 multiplies the overflow surface region for time phases within a predetermined time period. That is, the center-of-mass detector unit 72 extracts all surface portions that experience overlapping in any of the time phases in the predetermined time period. Then, the center-of-mass detector unit 72 calculates a center of mass of the multiplied surface regions. As the predetermined period for this multiplication, it is preferable to use, for example, one heartbeat when the target tissue is a left ventricle of a heart.

Figure 7:
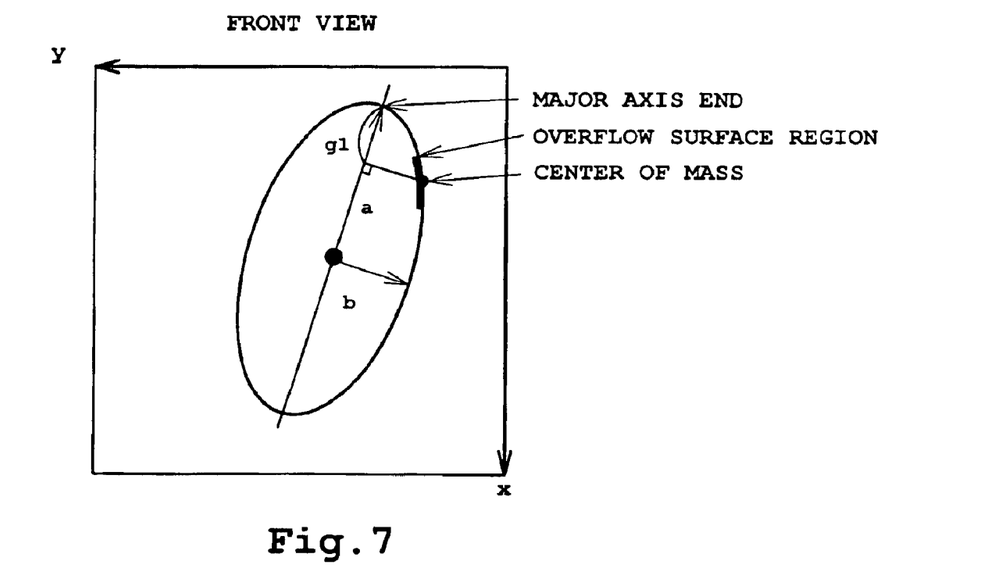
FIG. 7 is an explanatory diagram of calculation method of a major axis component.

The major axis component detector unit 74 calculates a major axis component based on the position of the center of mass output from the center-of-mass detector unit 72. An example calculation method of the major axis component will be described in the following while referring to FIG. 7. The major axis component detector unit 74 draws a perpendicular line from the center of mass of the surface region extending beyond the region of interest, hereafter referred to as the "overflow surface region", output from the center-of-mass detector unit 72 to the major axis of the region of interest, finds an intersection between this perpendicular line and the major axis, calculates a distance g1 between the found intersection and an end of the major axis residing on the side of the center of mass, and outputs the calculated results to the major/minor axes enlargement factor setting unit 80.

Referring again to FIG. 6, the front view minor component detector unit 76 draws a perpendicular line from the center of mass to the front view minor axis of the region of interest based on the position of the center of mass output from the center-of-mass detector unit 72, finds an intersection between the perpendicular line and the front view minor axis, calculates a distance g2 between that intersection and an end of the front view minor axis residing on the side of the center of mass, and outputs the calculated result to the major/minor axis enlargement factor setting unit 80. Similarly, the side view minor axis component detector unit 78 draws a perpendicular line from the center of mass to the side view minor axis of the region of interest based on the position of the center of mass output from the center-of-mass detector unit 72, finds an intersection between the perpendicular line and the side view minor axis, calculates a distance g3 between that intersection and an end of the side view minor axis residing on the side of the center of mass, and outputs the calculated result to the major/minor axes enlargement factor setting unit 80.

The major/minor axes enlargement factor setting unit 80 determines enlargement factors for the major axis and two minor axes based on values of g1, g2, and g3 output respectively from the major axis component detector unit 74, front view minor axis component detector unit 76, and side view minor axis component detector unit 78. The enlargement factors are preset based on the magnitude of the values of g1, g2, and g3. For example, when g1 is less than or equal to ¼ of the major axis radius a, it is determined that the overflow surface region is present in the proximity of the end of the major axis and the major axis radius is increased by 20%. When g1 is greater than ¼ of the major axis radius a, but is no more than ½ of the major axis radius a, it is determined that the overflow surface region is proximate to the end of the major axis, but not to a great degree and the major axis radius is increased by 10%. Similarly, the enlargement factors for the front view minor axis radius and the side view minor axis radius are determined based on the magnitudes of the values of g2 and g3. The enlargement factors of the axes set by the major/minor axes enlargement factor setting unit 80 are output to the major/minor axes setting unit (reference numeral 40 of FIG. 1) and the axes are enlarged.

The major/minor axes setting unit 40 shown in FIG. 1 outputs the enlarged lengths of the major axis, of the front view minor axis, and of the side view minor axis to the region-of-interest generator unit 42, which then creates an enlarged region of interest and outputs the generated region to the region-of-interest fit judging unit 52. In this manner, by repeatedly enlarging and correcting the major and minor axes, a three-dimensional region of interest in which the target tissue does not overflow can be generated. It is preferable that the region-of-interest corrector 60 also has a functionality to stop automatic correction in response to an instruction from the user. With such functionality, even when a particular site of the target tissue extends beyond the region of interest, the user can determine whether this site substantially influences the diagnosis, and can fix the region of interest accordingly.

The three-dimensional region of interest produced in the region-of-interest generator unit 42 is also output to a volume measuring unit 62. The volume measuring unit 62 measures the volume of the target tissue within the three-dimensional region of interest in each time phase by counting the number of target tissue voxels within the three-dimensional region of interest based on the binarized image output from the binarization processor unit 54. The measurement results of the volume of the target tissue obtained for the time phases are output to a graph formation unit 64 where a graph showing the volume of the target tissue in each time phase, that is, the measured time and the volume value, is created and output to the display 22 via the display image formation unit 20. The graph formation unit 64 may also create a graph of, for example, the rate of change of the volume by calculating the change rate based on the measurement results of volume for the time phases.

As described, the region-of-interest fit judging unit 52 applies a coloring process to the overflow surface region to form an image which explicitly shows that the target tissue extends beyond the region of interest and outputs this image to the display image formation unit 20. The display image formation unit 20 combines the three-dimensional ultrasonic image output from the coordinate converter unit 16 and the region of interest surface in which a coloring process is applied to the overflow surface region and displays the combined image to the display 22.

Figure 8:
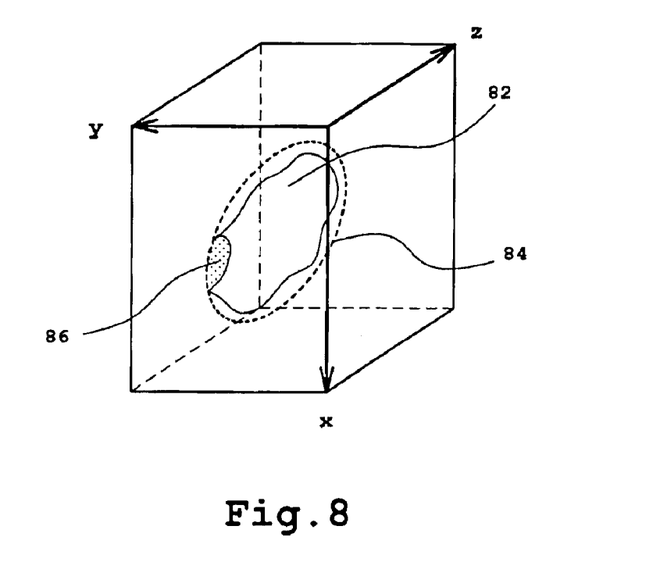
FIG. 8 is a diagram showing a target tissue image displayed on a display.

FIG. 8 is a diagram showing an example target tissue image displayed on a display 22 of the ultrasonic diagnostic device of FIG. 1. The target tissue image 82 is shown with a coloring process applied to a portion 86 extending beyond the three-dimensional region of interest 84. The user can see which part of the target tissue extends beyond the region of interest by viewing the displayed image.

In the preferred embodiment of the present invention shown in FIG. 1, it is even more preferable that a translational and rotational movement canceling processor unit be provided immediately after the coordinate converter unit 16.

Figure 9:
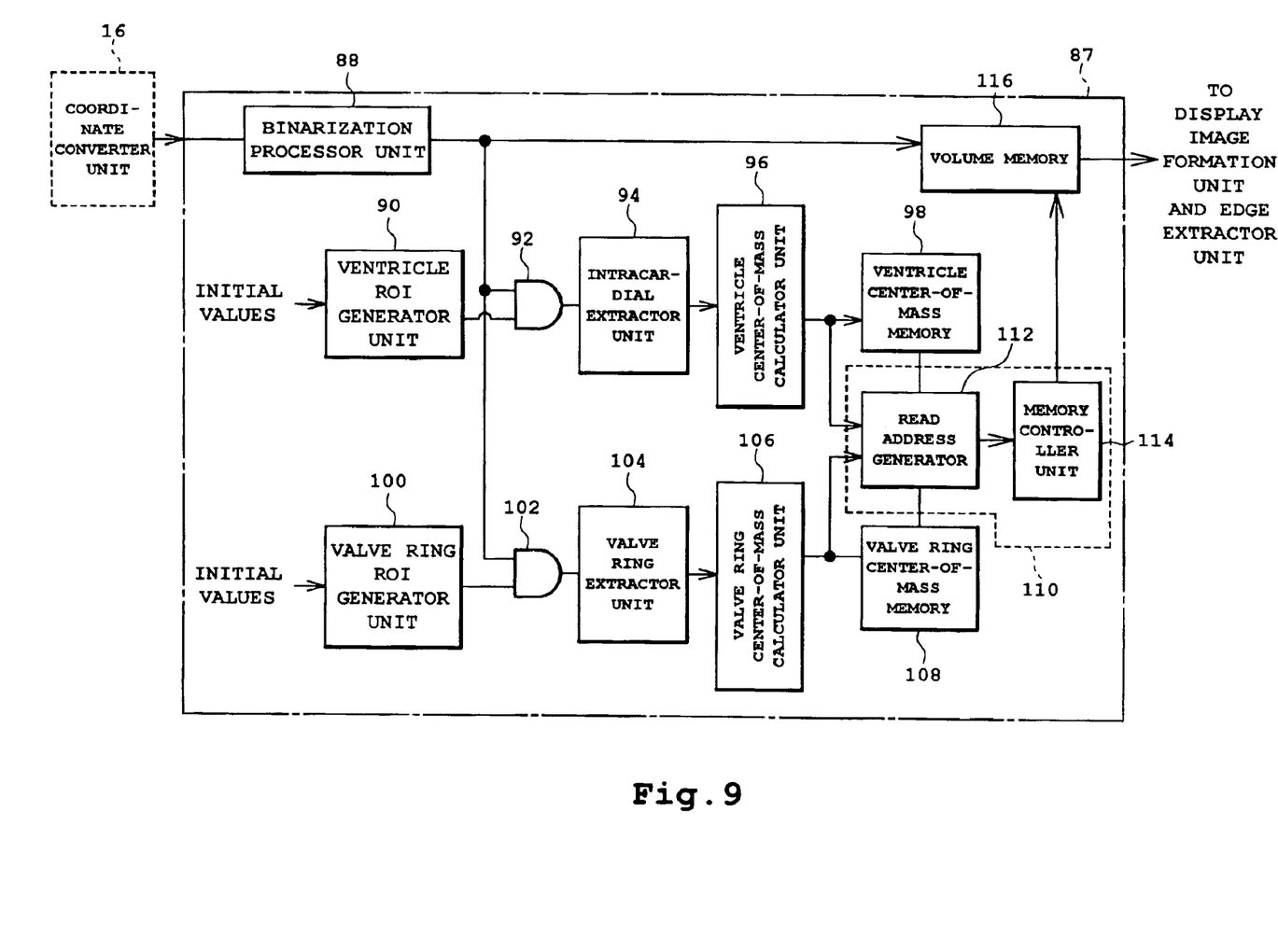
FIG. 9 is a block diagram showing an internal structure of a translational and rotational movement canceling processor unit.

FIG. 9 is a block diagram showing an internal structure of a translational and rotational movement canceling processor unit 87. The three-dimensional ultrasonic image output from the coordinate converter unit 16 is input to the translational and rotational movement canceling processor unit 87. At a binarization processor 88, a binarized image is formed in which voxels corresponding to the target tissue (target tissue voxels) and voxels corresponding to sites other than the target tissue (non-target tissue voxels) are distinguished.

A ventricular ROI (region of interest) generator unit 90 generates coordinates of an ROI which forms the outer periphery of the ventricle of a heart which is the target tissue. The ventricular ROI has a shape of, for example, an ellipse and the user sets initial values such as the lengths of the major and minor axes of the ellipse, position of the center, and the slope of the ellipse while viewing the ultrasonic image so that the image of the ventricle fits within the ROI. In this process, the user inputs the initial values using a trackball or the like by viewing the ultrasonic images and observing movement for one heartbeat so that the ROI contains the left ventricle of the heart in all time phases. The setting of the ROI is not limited to manual setting by the user, and may also be automatically set in response to the movement of the ventricle.

A ventricular gate circuit 92 is a circuit which allows only voxel data within the ventricular ROI to pass. Specifically, coordinates of the ROI output from the ventricular ROI generator 90 are input to one input terminal of the ventricular gate circuit 92 and the ventricular gate circuit 92 extracts only the voxel data of coordinates within the ventricular ROI in the binarized image input to the other input terminal, and outputs the extracted data to an intracardial extractor unit 94. The intracardial extractor unit 94 extracts an intracardial image inside the ventricle from the binarized image within the ROI. A ventricle center-of-mass calculator unit 96 calculates, for each time phase, coordinates of the center of mass within the image of the inside of the ventricle output from the intracardial extractor unit 94. The calculated coordinates of the center of mass of the ventricle are output to a read address generator 112 and a ventricle center-of-mass memory 98.

A valve ring section ROI (region of interest) generator unit 100 generates coordinates of an ROI forming an outer periphery of a valve ring section positioned at the end of the ventricle. The valve ring section ROI has a shape of, for example, an ellipse, and the user sets the initial values such as the lengths of the major and minor axes of the ellipse, position of the center, and the slope of the ellipse while viewing the ultrasonic image so that the image of the valve ring section fits within the ROI. In this process, the user sets the initial values using a trackball or the like while viewing ultrasonic images and observing movement for one heartbeat so that the ROI contains the valve ring section in all time phases. The setting of the ROI is not limited to manual setting by the user and may instead be mechanically set in response to the movement of the valve ring section.

A valve ring section gate circuit 102 is a circuit which allows only the voxel data within the ROI for the valve ring section to pass. Specifically, coordinates of ROI output from the valve ring section ROI generator 100 are input to one input terminal of the valve ring section gate circuit 102, and only the voxel data associated with coordinates within the valve ring section ROI are extracted from the binarized image input to the other input terminal and output to a valve ring section extractor unit 104. The valve ring section extractor unit 104 extracts a valve ring section image from the binarized image within the ROI. A valve ring section center-of-mass calculator unit 106 calculates, for each time phase, the coordinates of a center of mass of the valve ring section with respect to the valve ring section image output from the valve ring section extractor unit 104. The calculated coordinates of the center of mass of the valve ring section are output to the read address generator 112 and a valve ring center-of-mass memory 108.

The ventricle center-of-mass memory 98 stores coordinates of the center of mass of the ventricle at the point of telediastolic of the ventricle. An R wave of an cardiographic waveform is used as the trigger for indicating the point of telediastolic. In other words, along with the R wave obtained at the point of telediastolic as a trigger, the coordinates of the center of mass of the ventricle output from the ventricle center-of-mass calculator unit 96 are stored as coordinates of the center of mass of the ventricle at the point of telediastolic. Similarly, using the R wave as a trigger, coordinates of the center of mass of the valve ring section at the point of telediastolic are stored in the ventricle center-of-mass memory 108 from the ventricle center-of-mass calculator unit 106.

A read controller unit 110 comprises a read address generator unit 112 and a memory controller unit 114 and reads voxel data from a volume memory 116 in order to form an ultrasonic image in which the translational and rotational movements of the ventricle between volumes in each time phase are cancelled. More specifically, the read address generator 112 obtains coordinates of the center of mass of the ventricle at the point of telediastolic from the ventricle center-of-mass memory 98 and coordinates of the center of mass of the valve ring section at the point of telediastolic from the valve ring section center-of-mass memory 108. In addition, the read address generator unit 112 obtains the coordinates of the center of mass of the ventricle in the current volume from the ventricle center-of-mass calculator unit 96 and coordinates of the center of mass of the valve ring section in the current volume from the valve ring section center-of-mass calculator unit 106.

The read address generator unit 112 calculates a read address such that the center of mass of the ventricle of the current volume overlaps the center of mass of the ventricle at the telediastolic point and a straight line passing through the center of mass of the ventricle and the center of mass of the valve ring section in the current volume overlaps a straight line passing through the center of mass of the ventricle and the center of mass of the valve ring section at the telediastolic point.

A copy of voxel data output from the binarization processor unit 88 is stored in the volume memory 116 for each volume in the form of the unchanged address of the original image and the memory controller unit 114 reads voxel data from the volume memory 116 according to a read address calculated by the read address generator unit 112 and outputs the read voxel data to a display image formation unit (reference numeral 20 in FIG. 1) and the edge extractor unit (reference numeral 24 in FIG. 1). As a result, in an ultrasonic image based on the voxel data output from the volume memory 116, translational and rotational movements, relative to the whole human body, of the left ventricle of the heart which is the target tissue are cancelled out.

A preferred embodiment of the present invention has been described. This embodiment, however, is for exemplifying purpose only and should in no way be interpreted as limiting or restricting the scope of the present invention.

What is claimed is:

1. An ultrasonic diagnostic device comprising:
    a volume data formation unit for transmitting and receiving an ultrasonic wave to and from a three-dimensional space containing a target tissue to form volume data composed of a plurality of sets of voxel data;
    a reference line setting unit for setting a first reference line passing through the target tissue based on a plurality of planes set within the three-dimensional space and which intersect each other;
    a boundary finding unit for finding a boundary of the target tissue by referring to voxel data along the first reference line and a second reference line intersecting the first reference line;
    a shape parameter calculator unit for calculating a plurality of shape parameters for specifying a three-dimensional region of interest related to the target tissue based on the found boundary; and
    a region-of-interest setting unit for setting the region of interest within the three-dimensional space based on the plurality of shape parameters.

2. An ultrasonic diagnostic device according to claim 1, further comprising:
    a reference point setting unit for setting a reference point determined based on a structure of the target tissue, wherein
    the reference line setting unit sets a slope of the first reference line passing through the reference point.

3. An ultrasonic diagnostic device according to claim 2, further comprising:
    a plane image formation unit for forming a plane image containing the target tissue on each of the planes based on the volume data, wherein
    the reference point setting unit sets the reference point based on reference point setting information input by the user using each of the plane images displayed on a display.

4. An ultrasonic diagnostic device according to claim 3, wherein
    the reference line setting unit sets a slope of the first reference line based on reference line slope information input by the user using each of the plane images displayed on a display, the reference line slop information representing a slope of a projection line of the first reference line projected onto each of the plane images.

5. An ultrasonic diagnostic device according to claim 2, wherein
the reference point setting unit sets a center of mass of the target tissue which is calculated based on the volume data as the reference point.

6. An ultrasonic diagnostic device according to claim 5, wherein
the reference line setting unit sets a slope of the first reference line based on boundary information of the target tissue obtained using the volume data.

7. An ultrasonic diagnostic device according to claim 2, wherein
a plurality of second reference lines are set which is orthogonal to the first reference line and which passes through the reference point.

8. An ultrasonic diagnostic device according to claim 1, wherein
the plurality of planes are orthogonal to each other.

9. An ultrasonic diagnostic device according to claim 1, wherein
the second reference line is orthogonal to the first reference line.

10. An ultrasonic diagnostic device comprising:
a volume data formation unit for transmitting and receiving an ultrasonic wave to and from a three-dimensional space containing a target tissue to form volume data composed of a plurality of sets of voxel data;
a plane setting unit for setting three planes which are orthogonal to each other within the three-dimensional space;
a first reference line setting unit for setting a first reference line passing through the target tissue based on projected lines of the first reference line projected onto each of two planes of the three planes;
a second reference line setting unit for setting a second reference line which is orthogonal to the first reference line in one of the planes onto which the first reference lines is projected;
a third reference line setting unit for setting a third reference line which is orthogonal to the first reference line in the other of the planes onto which the first reference line is projected;
a reference line end calculator unit for calculating, based on the voxel data, a first reference line end which is an intersection of the first reference line and the boundary of the target tissue, a second reference line end which is an intersection between the second reference line and the boundary of the target tissue, and a third reference line end which is an intersection between the third reference line and the boundary of the target tissue;
an axes setting unit for setting a first axis based on the first reference line end and having a predetermined length on the first reference line, a second axis based on the second reference line end and having a predetermined length on the second reference line, and a third axis based on the third reference line end and having a predetermined length on the third reference line; and
a region-of-interest setting unit for setting a region of interest having an ellipsoidal shape in the three-dimensional space based on the set first, second, and third axes.

11. An ultrasonic diagnostic device according to claim 10, further comprising:
a plane image formation unit for forming a plane image containing the target tissue on each of the planes based on the volume data; and a reference point setting unit for setting, based on reference point setting information input by the user using each of the plane images displayed on a display, a reference point determined based on a structure of the target tissue; wherein
the first reference line setting unit sets the first reference line passing through the reference point based on a slope angle of the projected line input by the user using each of the plane images displayed on the display, and
the second and third reference lines pass through the reference point.

12. An ultrasonic diagnostic device according to claim 11, wherein
the plane setting unit determines positions of the three planes based on positional information of each plane input by the user; and
the plane image formation unit forms, as the plane image, a cross sectional image of the target tissue on each of the planes.

13. An ultrasonic diagnostic device according to claim 12, wherein
the axes setting unit sets, as the lengths of the first, second, and third axes, a length in which each axis exceeds the boundary of the target tissue and projects outside, and
the region-of-interest setting unit sets a region of interest having an ellipsoidal shape and surrounding the inside of the boundary of the target tissue.

14. An ultrasonic diagnostic device according to claim 13, further comprising:
a region-of-interest judging unit for judging, based on the volume data and the region of interest, that the inside of the boundary of the target tissue extends beyond the region of interest.

15. An ultrasonic diagnostic device according to claim 14, wherein
the region-of-interest judging unit judges that the inside of the boundary of the target tissue extends beyond the region of interest when a voxel inside the boundary of the target tissue is on the surface of the region of interest.

16. An ultrasonic diagnostic device according to claim 15, further comprising:
a region-of-interest corrector unit for re-setting the lengths of the first axis, of the second axis, and of the third axes when the inside of the boundary of the target tissue extends beyond the region of interest.

17. An ultrasonic diagnostic device according to claim 16, wherein
the region-of-interest corrector unit re-sets the lengths of the first axis, of the second axis, and of the third axis based on the position of the overflowing portion of the inside of the boundary of the target tissue on the surface of the region of interest.

18. An ultrasonic diagnostic device according to claim 17, further comprising:
an overflow image formation unit for forming an overflow image in which a predetermined display process is applied to the overflowing portion of the inside of the boundary of the target tissue on the surface of the region of interest.

* * * * *